(12) United States Patent
Chappel

(10) Patent No.: US 9,971,358 B2
(45) Date of Patent: May 15, 2018

(54) ADJUSTABLE PASSIVE FLOW REGULATOR

(71) Applicant: DEBIOTECH S.A., Lausanne (CH)

(72) Inventor: Eric Chappel, Versonnex (FR)

(73) Assignee: DEBIOTECH S.A., Lausanne (CH)

( * ) Notice: Subject to any disclaimer, the term of this patent is extended or adjusted under 35 U.S.C. 154(b) by 251 days.

(21) Appl. No.: 14/759,299

(22) PCT Filed: Jan. 10, 2014

(86) PCT No.: PCT/IB2014/058180
§ 371 (c)(1),
(2) Date: Jul. 6, 2015

(87) PCT Pub. No.: WO2014/108860
PCT Pub. Date: Jul. 17, 2014

(65) Prior Publication Data
US 2015/0346732 A1   Dec. 3, 2015

(30) Foreign Application Priority Data
Jan. 10, 2013   (EP) ..................................... 13150888

(51) Int. Cl.
*G05D 7/01* (2006.01)
*A61M 5/168* (2006.01)
*A61M 27/00* (2006.01)

(52) U.S. Cl.
CPC ....... *G05D 7/0113* (2013.01); *A61M 5/16881* (2013.01); *A61M 27/006* (2013.01); *Y10T 137/7922* (2015.04)

(58) Field of Classification Search
CPC . G05D 7/012; G05D 7/0113; A61M 5/16881; A61M 27/006; Y10T 137/7785; Y10T 137/7792
See application file for complete search history.

(56) References Cited

U.S. PATENT DOCUMENTS

| | | | |
|---|---|---|---|
| 3,401,719 A | 9/1968 | Rosser | |
| 3,768,508 A | 10/1973 | Schulte | |
| 3,886,968 A * | 6/1975 | Murrell ................ | G05D 7/0113 137/504 |
| 4,551,128 A | 11/1985 | Hakim et al. | |
| 4,625,759 A | 12/1986 | Craig | |
| 4,646,781 A | 3/1987 | McIntyre et al. | |
| 5,725,017 A | 3/1998 | Elsberry et al. | |
| 5,839,467 A | 11/1998 | Saaski et al. | |

(Continued)

FOREIGN PATENT DOCUMENTS

| CN | 1894524 A | 1/2007 |
|---|---|---|
| CN | 102105184 A | 6/2011 |

(Continued)

OTHER PUBLICATIONS

International Search Report for PCT/IB2014/058180, dated Apr. 23, 2014, 4 pages.

(Continued)

*Primary Examiner* — Eric Keasel
(74) *Attorney, Agent, or Firm* — Nixon & Vanderhye P.C.

(57) ABSTRACT

An adjustable passive flow regulator may be used in the field of drug delivery (liquid or gaseous, e.g. for pain management) or for draining cerebrospinal fluid (CSF) for hydrocephalus patient.

20 Claims, 10 Drawing Sheets

(56) References Cited

U.S. PATENT DOCUMENTS

| | | |
|---|---|---|
| 6,179,586 B1 | 1/2001 | Herb et al. |
| 6,203,523 B1 | 3/2001 | Haller et al. |
| 6,237,619 B1 | 5/2001 | Maillefer et al. |
| 6,276,491 B1 | 8/2001 | Schönfeld |
| 6,382,588 B1 | 5/2002 | Hierold |
| 6,830,229 B2 | 12/2004 | Wetzel et al. |
| 6,986,365 B2 | 1/2006 | Henning et al. |
| 7,832,429 B2 | 11/2010 | Young et al. |
| 8,211,060 B2 | 7/2012 | Steinbach |
| 8,276,618 B2 | 10/2012 | Cewers |
| 8,539,981 B2 | 9/2013 | Chappel |
| 8,858,491 B2 | 10/2014 | Field et al. |
| 2005/0054988 A1 | 3/2005 | Rosenberg et al. |
| 2005/0273081 A1 | 12/2005 | Olsen |
| 2006/0206049 A1 | 9/2006 | Rodgers et al. |
| 2008/0154215 A1 | 6/2008 | Rosenberg et al. |
| 2008/0249510 A1 | 10/2008 | Mescher et al. |
| 2009/0202391 A1 | 8/2009 | Hagiwara et al. |
| 2010/0028170 A1 | 2/2010 | Schneeberger et al. |
| 2010/0324504 A1 | 12/2010 | Chappel et al. |

FOREIGN PATENT DOCUMENTS

| | | |
|---|---|---|
| DE | 42 23 067 A1 | 1/1994 |
| DE | 10 2005 058 080 A1 | 6/2007 |
| EP | 0 156 974 A2 | 10/1985 |
| EP | 0 369 712 A2 | 5/1990 |
| EP | 1 512 422 A1 | 3/2005 |
| EP | 2 359 886 | 8/2011 |
| FR | 2 905 429 A1 | 3/2008 |
| JP | 60-139257 A | 7/1985 |
| JP | 5-508906 A | 12/1993 |
| JP | 2007-509286 A | 4/2007 |
| WO | 92/14199 A1 | 8/1992 |
| WO | WO 99/38552 | 8/1999 |
| WO | 99/53205 A1 | 10/1999 |
| WO | 2005/033561 A2 | 4/2005 |
| WO | WO 2007/004105 | 1/2007 |
| WO | 2008/004572 A1 | 1/2008 |
| WO | 2008/094672 A2 | 8/2008 |
| WO | WO 2009/098314 | 8/2009 |
| WO | 2010/020891 A1 | 2/2010 |

OTHER PUBLICATIONS

Written Opinion of the ISA for PCT/IB2014/058180, dated Apr. 23, 2014, 3 pages.

* cited by examiner

US 9,971,358 B2

ADJUSTABLE PASSIVE FLOW REGULATOR

This application is the U.S. national phase of International Application No. PCT/IB2014/058180 filed 10 Jan. 2014, which designated the U.S. and claims priority to EP Patent Application No. 13150888.9 filed 10 Jan. 2013, the entire contents of each of which are hereby incorporated by reference.

FIELD OF INVENTION

The present invention is related to an adjustable passive flow regulator which may be used in the field of drug delivery (liquid or gaseous, e.g. for pain management) or for draining cerebrospinal fluid (CSF) for hydrocephalus patient.

STATE OF THE ART

Passive drug infusion devices, in contrast to active ones, do not rely on a pump to deliver a drug but rather on a pressurized drug reservoir. A known problem of these passive devices is that the drug flow rate to a delivery location, which may be a patient's body for instance, may vary as a function of the amount of drug remaining in the reservoir as far as the pressure in the reservoir depends on this amount. Such passive devices are thus usually provided with a fluid flow regulator to ensure that the drug flow rate is as constant as possible with respect to the amount of drug remaining in the reservoir.

An example of such a passive drug flow regulator is available by the Applicant under the registered name "Chronoflow" and is disclosed in U.S. Pat. No. 6,203,523. The contents of the U.S. Pat. No. 6,203,523 are incorporated by reference in the present account. This device comprises a fluid inlet adapted to be connected to a fluid reservoir and a fluid outlet adapted to be connected to a patient's body. It comprises a rigid substrate and a resilient membrane tightly linked together in peripheral linking areas so as to define a cavity there between. This cavity is connected to the fluid outlet while the membrane has a first surface opposite the cavity which is connected to the fluid inlet. The membrane has a central through hole contiguous with the cavity, to define a pathway for a fluid from the fluid inlet to the fluid outlet, and is flexible so as to be able to come into contact with the substrate, in case a fluid would apply a pressure on the first surface that would be larger than a first predefined threshold value. As the membrane would come into contact with the substrate in the region of its central through hole, this would occlude the latter and result in hindering a fluid from flowing through it. This device further comprises a flow regulator open channel etched in the substrate with an inlet facing the central through hole of the membrane and an outlet connected to the outlet of the device. This channel is in the shape of a spiral curve such that, the more pressure is applied against the membrane, the more it closes the channel thus forcing the fluid to flow in it to find its way out of the cavity. Consequently, when the pressure applied on the membrane increases, the length of the fluid pathway located within the flow regulator channel increases and so does the fluidic resistance of the device. Thus, the flow rate may be kept approximately constant within a predefined range in terms of the reservoir pressure.

However, fabrication of such a device is complicated and expensive. Indeed, the substrate has to be etched according to a specific pattern, which is rather delicate regarding the accuracy level that has to be respected for the flow regulation to operate properly. Thus, not only the manufacture of the substrate requires specific extra-steps, but also these steps are further delicate to carry out. Depending on the dimensions of the device, specific materials such as Sal is to be used for manufacture of the substrate, which is still more expensive. It is also important to note that this device is sensitive to particles. The large contact area between the membrane and the substrate at high pressure can be problematic since any particle in this area will induce a leakage. Moreover, the device manufactured through this process is then designed for one specific set of parameters regarding delivery of a drug, i.e. predefined reservoir pressure range and average flow rate. Complex fluidic simulations of such device are necessary to estimate the spiral shape and to take into account the flow restriction outside of the channel, making any design change difficult.

Park reports another constant flow-rate microvalve for hydrocephalus treatment [S. Park, W. H. Ko, and J. M. Prahl, "A constant flow-rate microvalve actuator based on silicon and micromachining technology," in Tech. Dig. 1988 Solid-State Sens. Actuator Workshop (Hilton Head '88), Hilton Head Island, S.C., Jun. 6-9 (1988) 136-139]. The valve is also made of a diaphragm covering a flat substrate; the channel cross-section diminishes under increasing pressure, thus leading to quasi-steady flow-rate. Both theoretical and experimental data reported show that a perfectly steady rate cannot be achieved since the flow resistance should increase with the applied pressure in a linear manner and the change of the cross-section of the channel is strongly non-linear. This non-linearity is not compensated by the use of a spiral channel.

Kartalov reports a PDMS-based device for passive flow regulation of Newtonian fluid [E. P. Kartalov, C. Walker, C. R. Taylor, W. F. Anderson, and A. Scherer, "Microfluidic vias enable nested bioarrays and autoregulatory devices in Newtonian fluids," Proc. Nat. Acad. Set. 103 (2006) 12280-12284]. This device is made of a three-dimensional structure showing an important dead volume. The autoregulated device comprises a main channel between a source and an exhaust, the static pressure decreases as the fluid flows along this channel which also comprises a flexible membrane called pushup valve. The static pressure remains constant along the dead-end detour channel leading to the valve. The pushup valve experiences an effective pressure equal to the static pressure drop between the channel split and the main channel segment above the valve. As the pressure drop increases, the valve membrane deforms upward and constricts the main channel, leading to an increase of the fluidic resistance with applied pressure and thus to nonlinearity for Newtonian fluids. The presence of dead-ends for such devices makes the priming difficult. Air trapped below the valve would induce damping effect. But the main drawback of such devices is the flow-rate accuracy.

The application for which the publication number is WO 2007/004105 A1 discloses a valve device comprising a substrate and an elastic membrane. Said membrane is joined at least around a valve area to the substrate. Said valve comprises a pressure device which presses a plunger against the membrane to close the valve. So said valve is actuated by said pressure device and is not auto regulated depending on the fluid which flows trough said valve.

Saaski et al. disclose in U.S. Pat. No. 5,839,467 a device having a membrane tightly attached to a substrate that has a cavity and a central pillar having a through hole.

The inlet is located on the lateral side of the substrate. The contents of the U.S. Pat. No. 5,839,467 are incorporated by reference in the present account. The fluid flows from this inlet towards the outlet located after the through hole of the substrate pillar. The membrane side opposite to the pillar is submitted to the reservoir pressure. The small gap between the upper part of the pillar and the membrane forms a large fluidic restriction. By increasing the reservoir pressure the membrane deflects towards the pillar, reducing the gap height between the pillar and the membrane. The device can be considered as a valve which can shut off when the reservoir pressure increases, i.e. when the gap height between the pillar and the membrane becomes equal to zero. In that case, the pressures on both sides of the membrane are equal excepted above the pillar area. Various configurations including check-valve feature, shut-off feature, device having a membrane with a through hole and a non-drilled pillar are disclosed. For each proposal, the flow rate can be therefore more or less controlled up to the closing of the valve but in any case a constant flow rate can be achieved because of the non-linearity of the fluidic resistance of that valve as the gap height varies. Moreover, the fact that the reservoir pressure applies directly on both sides of the membrane makes necessary the use of a small gap between the pillar and the membrane at any pressure otherwise the device do not regulate the flow. The gap disclosed of only 2.5 microns is an illustration of this feature. The device is therefore very sensitive to particles. Relative machining tolerances for this gap are also difficult to achieve.

The application US 2011/132480 proposes an alternative passive fluid flow regulator which is easier and cheaper to manufacture and which would provide more flexibility as far as its conditions of use are concerned. The contents of the application US 2011/132480 are incorporated by reference in the present account. Said application US 2011/132480 discloses an invention include in particular a regulator characterized by the fact that its membrane comprises at least one additional through hole contiguous with the cavity and arranged such that a fluid may flow through it even in case it would apply a pressure on the membrane first surface that would be larger than a first predefined threshold value but smaller than a second predefined threshold value. This regulator is moreover characterized by the fact that the membrane and the additional through hole are further arranged so that a fluid flow rate would be substantially linear, preferably constant, as a function of the pressure applied on the membrane first surface in a range going approximately from the first to the second predefined threshold values. The membrane may comprise n additional through holes contiguous with the cavity, each j-th additional through hole being arranged such that a fluid may flow through it in case the fluid would apply a pressure on the first surface that would be larger than a j-th predefined threshold value but smaller than a (j+1)-th predefined threshold value. Again, the membrane and the n additional through holes would be further arranged so that a fluid flow rate would be substantially linear, preferably constant, as a function of the pressure applied on the first surface in a range going approximately from the first to the (n+1)-th predefined threshold values. But, after its manufacturing, this device cannot be adjusted as necessary to suit the particular needs of patient. Thus, each device is designed to a particular need and if the need changes, the device have to be changed too.

Passive flow regulators may advantageously be used in hydrocephalus treatment. Hydrocephalus is usually due to blockage of CSF outflow in the ventricles or in the subarachnoid space over the brain. Hydrocephalus treatment is surgical: it involves the placement of a ventricular catheter (a tube made of silastic for example) into the cerebral ventricles to bypass the flow obstruction/malfunctioning arachnoidal granulations and the draining of the excess fluid into other body cavities, from where said fluid can be resorbed. Most of the CSF shunts have been based on the principle of maintaining a constant intracranial pressure (ICP) regardless of the flow-rate of CSF. The CSF shunts have been constructed to cut off CSF-flow when the differential pressure between the inlet and the outlet of the CSF shunt was reduced to a predestined level, called the opening pressure of the shunt.

An example of an ICP shunt is shown in U.S. Pat. No. 3,288,142 to Hakim, which is a surgical drain valve device used to control the drainage of fluid between different portions of the body of a patient, particularly for draining cerebrospinal fluid from the cerebral ventricles into the blood stream (so called ventriculo-atriostomy). Clinical experience has proven that this principle of shunting is not an ideal solution. Sudden rises of the ICP, e.g. due to change of position, physical exercise, or pathological pressure waves result in excessive CSF drainage. Several reports in the literature (Aschoff et al., 1995) point at problems due to this over-drainage, and especially the pronounced narrowing of the ventricles has been pointed out as being the main factor leading to malfunctioning of the implanted shunting device. The reason is that the ventricular walls may collapse around the ventricular CSF shunt device, and particles (cells, debris) may intrude into the shunt device.

The devices described in the US patent applications US 2010/0324504, US 2012/0048403, US 2011/0132480 and US 2012/0316492 show alternative ways to regulate the CSF flow. The contents of the application US 2012/0316492 and US 2010/0324504 are incorporated by reference in the present account. This device allows having a large range of use and a good tolerance of particle. But one of the major drawbacks of theses valves lies in their lack of adjustment means. Unfortunately, the characteristics of the valve need to be adapted to each patient as a function of the natural characteristics of the patient's organism, and for any given patient, the characteristics of the valve need to be modified over time as a function of the way the disease evolves. Replacing one valve with another having different characteristics, whether for the purposes of initial adjustment or during evolution of the disease, requires a surgical operation to be performed since the valve is implanted beneath the skin of the patient. Because the normal ICP, for a given patient, is not known a priori, it is highly desirable to have a flow regulator having a flow rate that can be adjusted after implantation.

An adjustable valve is described in U.S. Pat. No. 4,551,128 to Hakim et al. The contents of the U.S. Pat. No. 4,551,128 are incorporated by reference in the present account. However, due to the elastomeric properties of the diaphragm material, maintenance of the implanted valve may be required. Further, flow rate adjustment of this adjustable valve after implantation may require a surgical procedure.

Another adjustable valve mechanism, described in U.S. Pat. No. 4,781,673 to Watanabe, includes two parallel fluid flow passages, with each passage including a flow rate regulator and an on-off valve. Fluid flow through the passages is manually controlled by palpably actuating the on-off valves through the scalp. Although the Watanabe device permits flow rate control palpably through the scalp and thus, without surgical intervention, patient and/or physician attention to the valve settings is required.

Several reports in the literature [Aschoff A et al., Conference Shunt Technology, Center of Devices and Radiological Health—Food and Drug Administration, Bethesda, Md., 8

Jan. 1999] point at problems due to this overdrainage, and especially the pronounced narrowing of the ventricles has been pointed out as being the main factor leading to malfunctioning of the implanted shunting device. The reason is that the ventricular walls may collapse around the ventricular CSF shunt device, and particles (cells, debris) may intrude into the shunt device. These devices are therefore very sensitive to particles and relative machining tolerances for this gap are also difficult to achieve. Several devices cannot be adjusted or are not easily adjustable.

Furthermore, typical passive flow regulators are based on variable fluidic restriction. The flow is usually laminar and varies linearly with the viscosity according to Poiseuille's law. For water, the effect of the temperature on viscosity is important, and such devices are usually intended for implantable application or infusion in a controlled environment like hospitals.

Thus, the major drawbacks of these valves lies in their lack of accuracy, their adjustable means, their sensitivity to particles, their range of use and/or their sensitivity to the temperature.

General Description of the Invention

In view of the foregoing, the main object of the present invention is to provide a new and improved pressure regulator valve which allows a good management of the predefined flow rate. The present invention improves the accuracy, the range of use, the adaptability during the therapy and decreases the sensitiveness to particles and some embodiment may decrease the sensitiveness to temperature.

The invention is set forth and characterized in the independent claim, while the dependent claims describe other characteristics of the invention.

The present invention unveils a passive flow regulator that can be adjusted during the therapy for example after implantation and/or automatically adjusted depending on the temperature. The principle of fluid flow regulation is based on elastic distortion of a membrane that goes into contact with a substrate as described in the patent applications US 2011/0132480 and US 2012/0316492, whose their contents are incorporated by reference in the present account. These flow regulators of the passive type comprising a fluid inlet which may be connected to a fluid reservoir and a fluid outlet which may be connected to a delivery location.

Said regulator comprises a substrate and a membrane tightly linked together in predefined linking areas so as to define a cavity there between. The cavity depth is limited by the lower face of the membrane and the upper face of the substrate. In other word, the cavity depth is the gap between said membrane and said substrate.

Said cavity is connected to said fluid outlet and to said fluid inlet. Furthermore said substrate and/or said membrane have a through hole contiguous with said cavity, to define a pathway for a fluid from said fluid inlet to said fluid outlet.

For clarity but not limited, the membrane face which faces cavity is called the lower face and the opposite face of the membrane called upper face. Said membrane or at least a part of said membrane is flexible in such a way that said lower face comes into contact with the substrate. Furthermore, the fluid exerts a pressure on the upper face of the membrane so the membrane flexes depending on the fluid pressure. Said membrane permits to regulate passively the flow depending of the fluid pressure. "Regulate passively" means the flow is regulated without any physical actuator.

When a pressure applied to the upper face is larger than a predefined threshold value, the flexible membrane is able to come into contact with at least a part of said substrate. The parts of said substrate and/or said membrane may comprise said through holes defining thereby a valve which may increase the fluidic resistance and may hinder a fluid from flowing through said through holes.

Advantageously, the substrate comprises a flexible part and a rigid part. In other word, said substrate is made of a rigid part (also called mesa) surrounded by a flexible part; said flexible part allowing the rigid part to move so as to increase or decrease the cavity depth.

In one embodiment, said rigid part may be pushed or pulled by an adjustment means, e.g. a preloaded spring, a plunger and/or a screw. Said adjustment means may be adjusted without contact using for example a magnetic rotor, the increase (resp. decrease) of the preload inducing an increase (resp. decrease) of said valve openings and therefore a decrease (resp. an increase) of the flow rate.

In another embodiment, a polymeric rod having a high CTE (Coefficient of Thermal Expansion) is attached to the substrate in such a way that an increase of the temperature induces a compression force against the substrate and reduces the gap between the membrane and said substrate. And/or, a decrease of the temperature may increase the cavity depth. Thus the valves of the system have a fluidic resistance for a given reservoir pressure and when the temperature increases, the device may compensate the reduction of the dynamic viscosity of the liquid. In other configuration the rod may be replaced by-morph systems.

Thus, this flow regulator comprises two distinct means for managing the flow rate. The first means is the flexible membrane which may come into contact with at least a part of said substrate for instance depending on the pressure applied to the upper face. Said first means is a passive means. And the second means increases or decreases the cavity depth thanks to the adjustment means which may be for example adjusted through an external action or automatically adjusted according to some external condition change. Said adjustment means is an active means. The object of these both means is to improve the accuracy flow rate while minimizing the impact caused by the effects of exogenous variables and/or to adjust the therapy to the different stages of the illness and/or to adapt the therapy or device to each patient as a function of the natural characteristics of the patient's organism.

LIST OF FIGURES

The present invention will be better understood at the light of the following detailed description which contains non-limiting examples illustrated by the following figures.

Figure 2A:
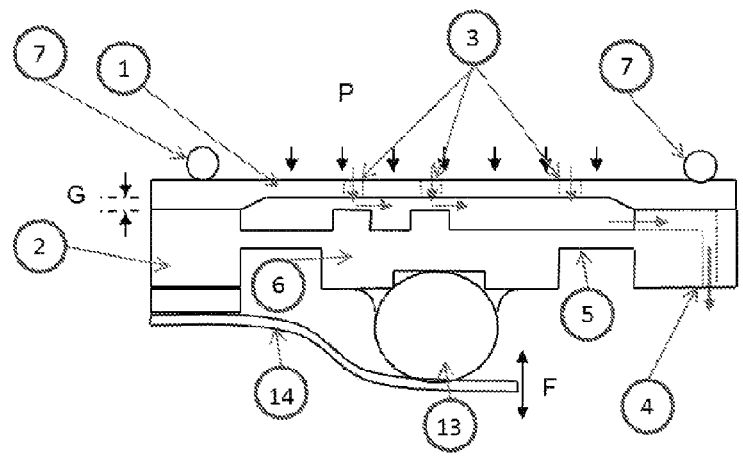
FIG. 2a shows an adjustable passive flow regulator with drilled membrane with a rigid ball glued on the mesa, the force being applied by a cantilever spring (blade).
Figure 2B:
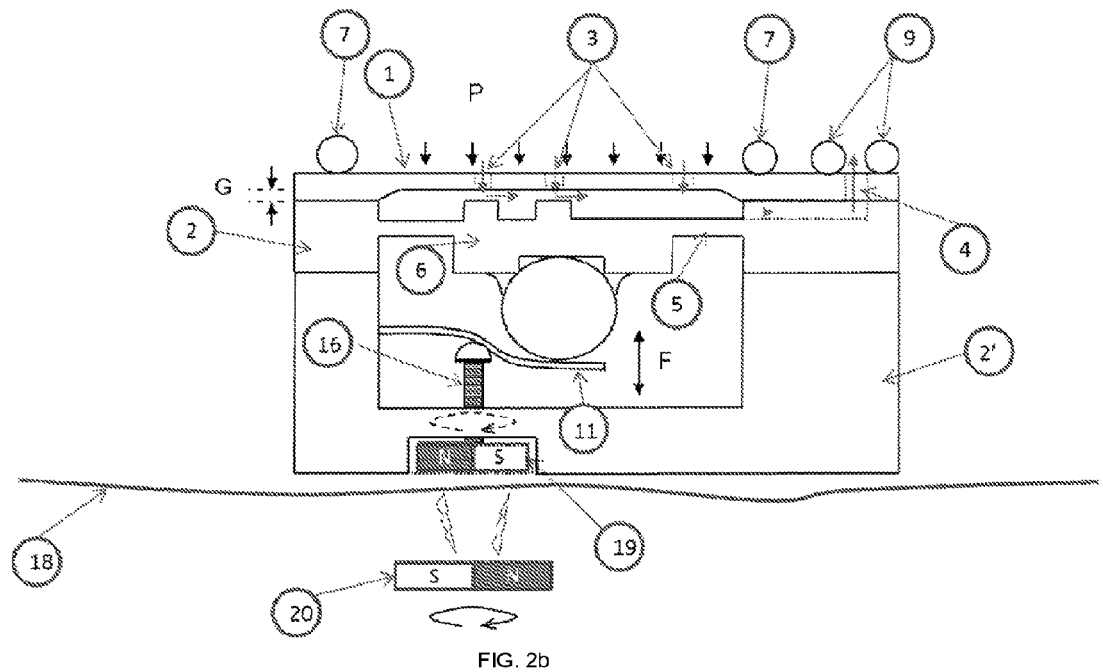
Figure 2C:
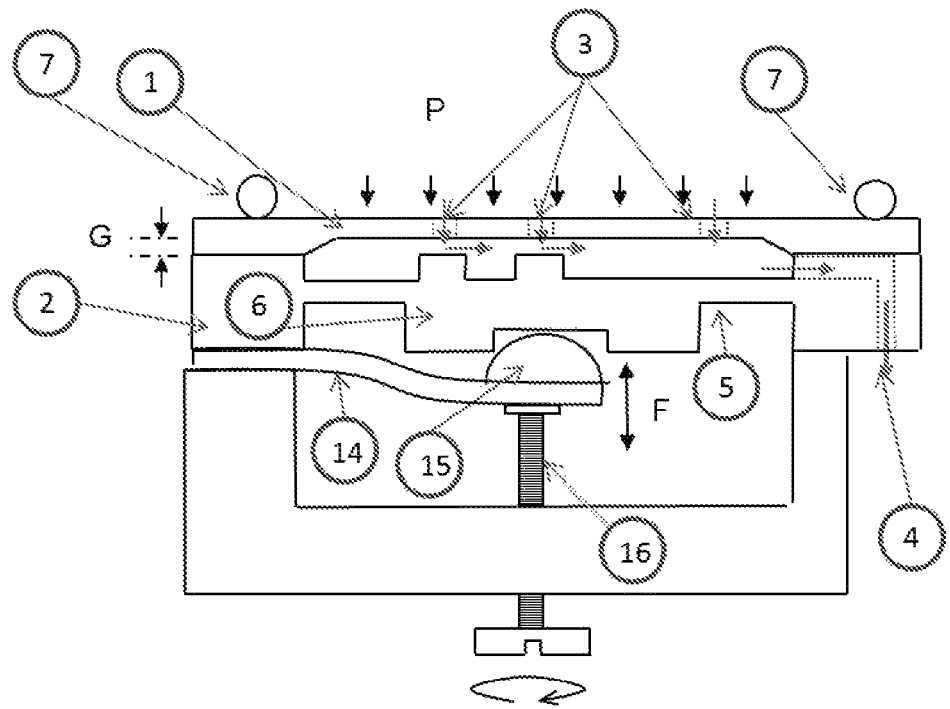
Figure 3A:
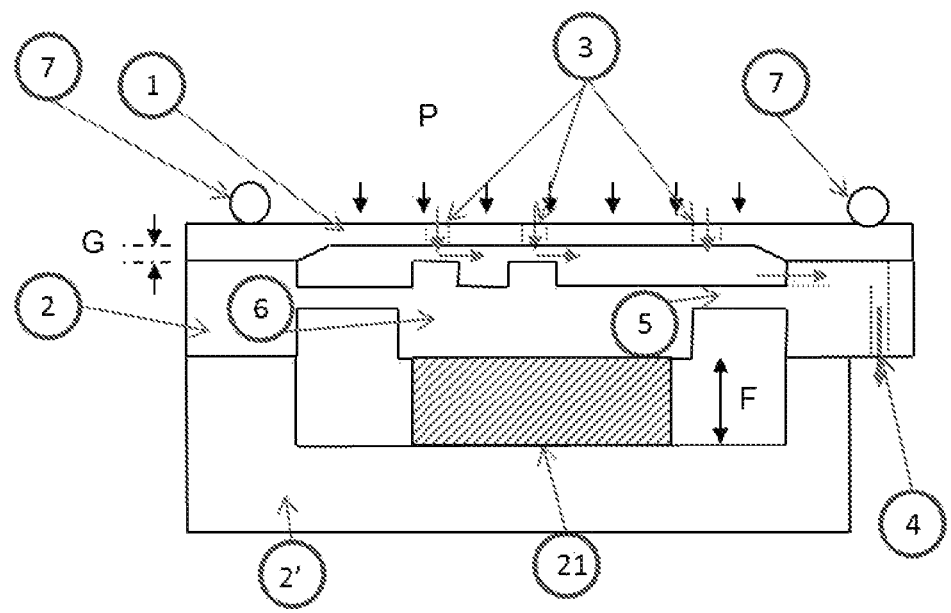
Figure 3B:
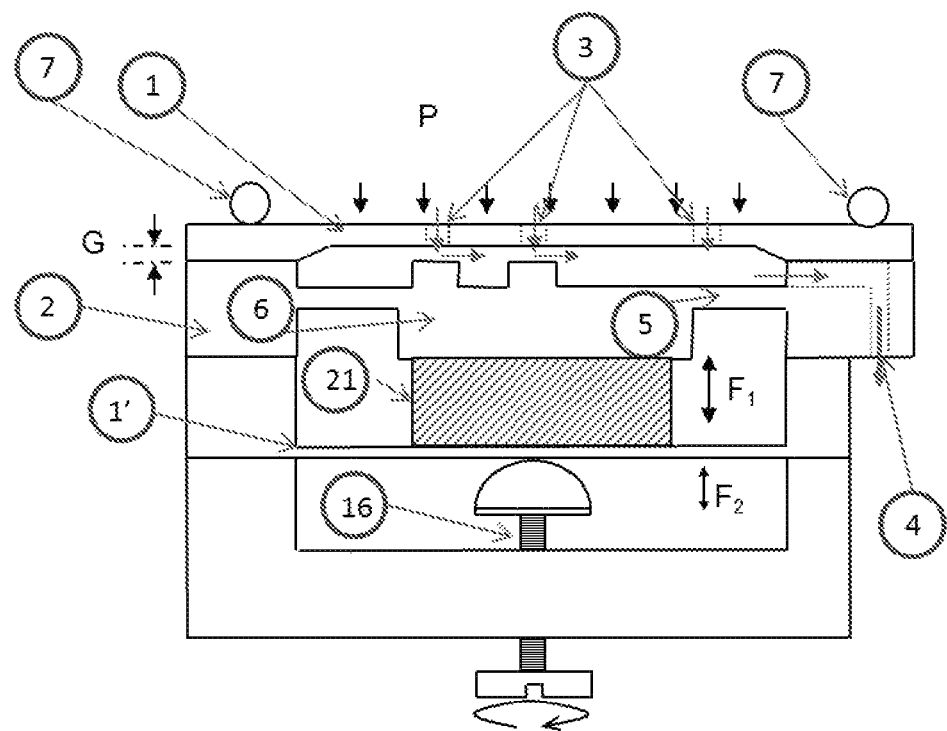
Figure 3C:
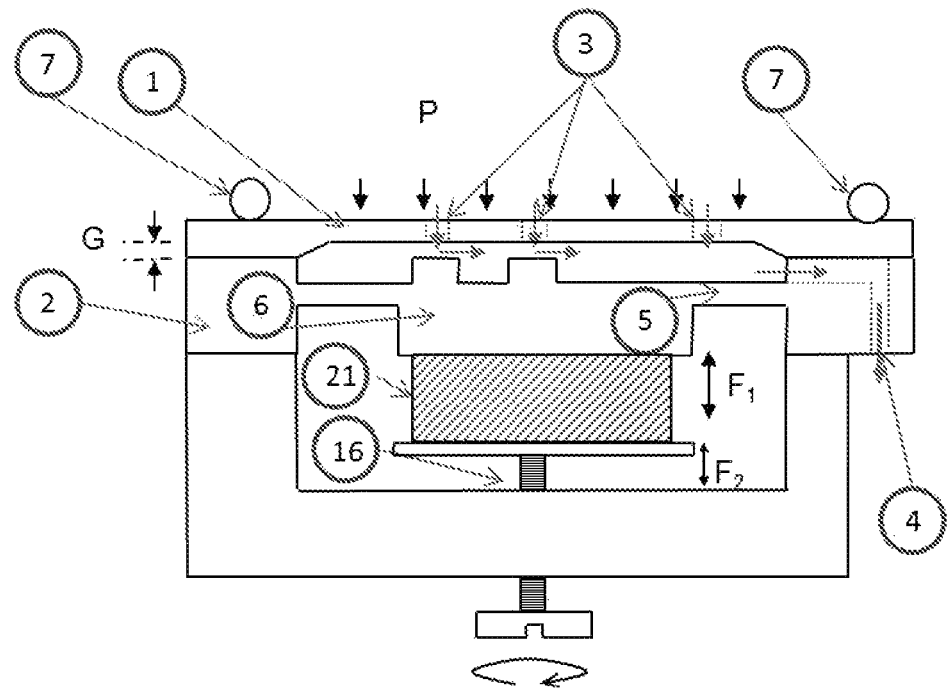
Figure 3D:
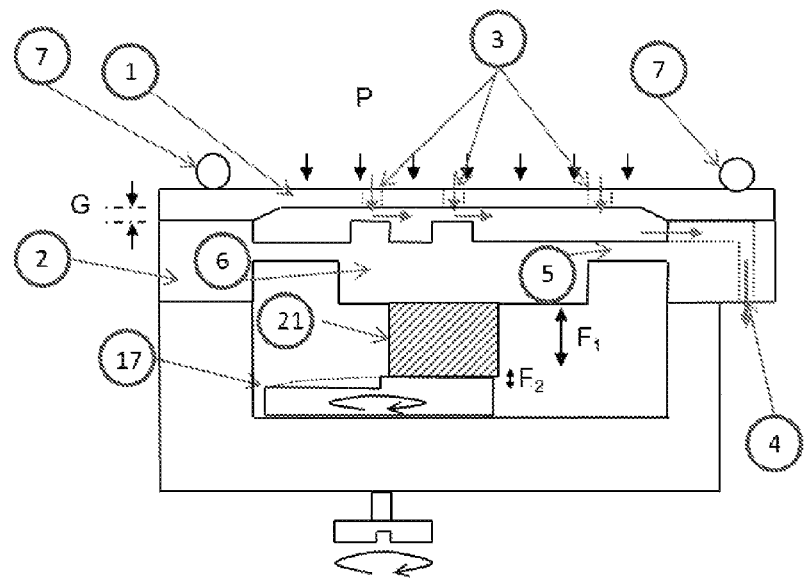
Figure 4:
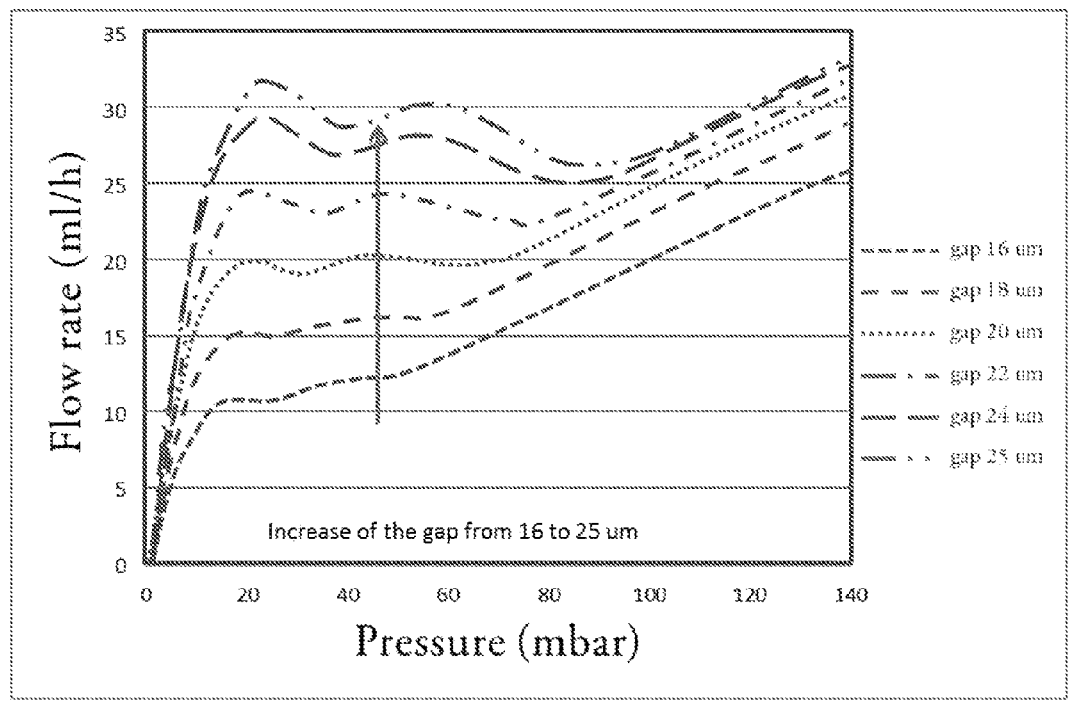

FIG. 2b shows the same embodiment of the FIG. 2a but with an adjustment means containing magnetic element FIG. 2c shows the same embodiment of the FIG. 2a but with a circular element fixe to the blade and a screw to adjust FIG. 3a shows an embodiment comprising a polymeric rod having a high Coefficient of Thermal Expansion FIGS. 3b, 3c and 3d show the same embodiment of the FIG. 3a but coupled with another adjustment means FIG. 4 shows the flow rate versus several cavity height (gap) flow regulator.

Figure 5:
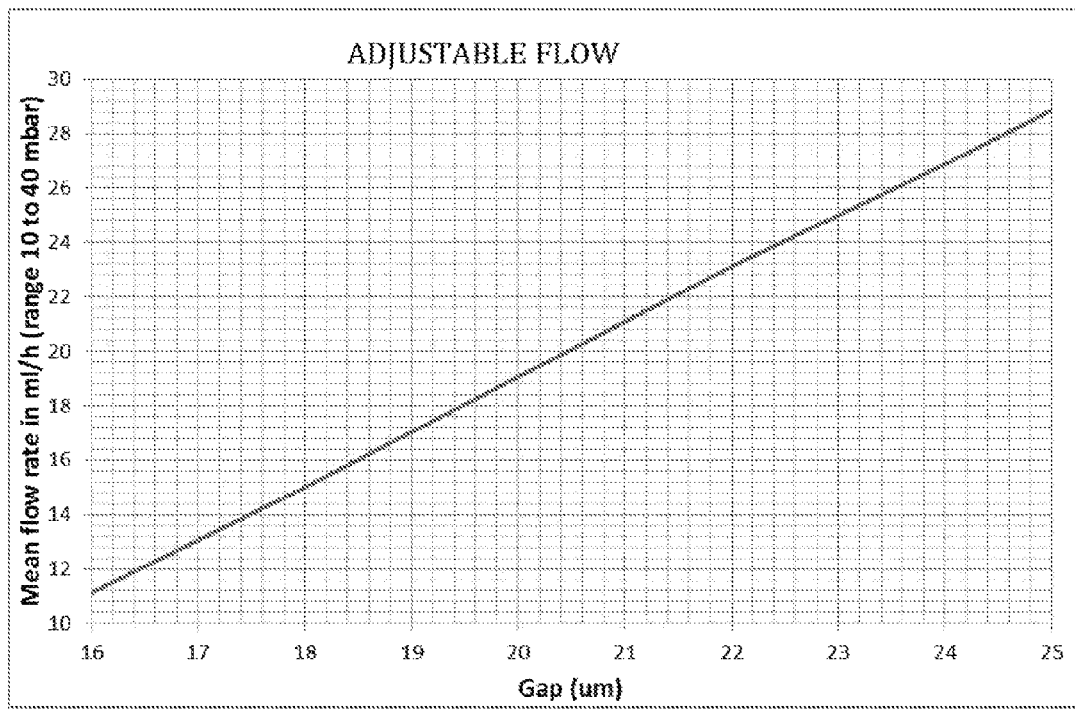

FIG. 5 shows means flow rate in the range 10 to 40 mbar versus the gap.

Figure 6:
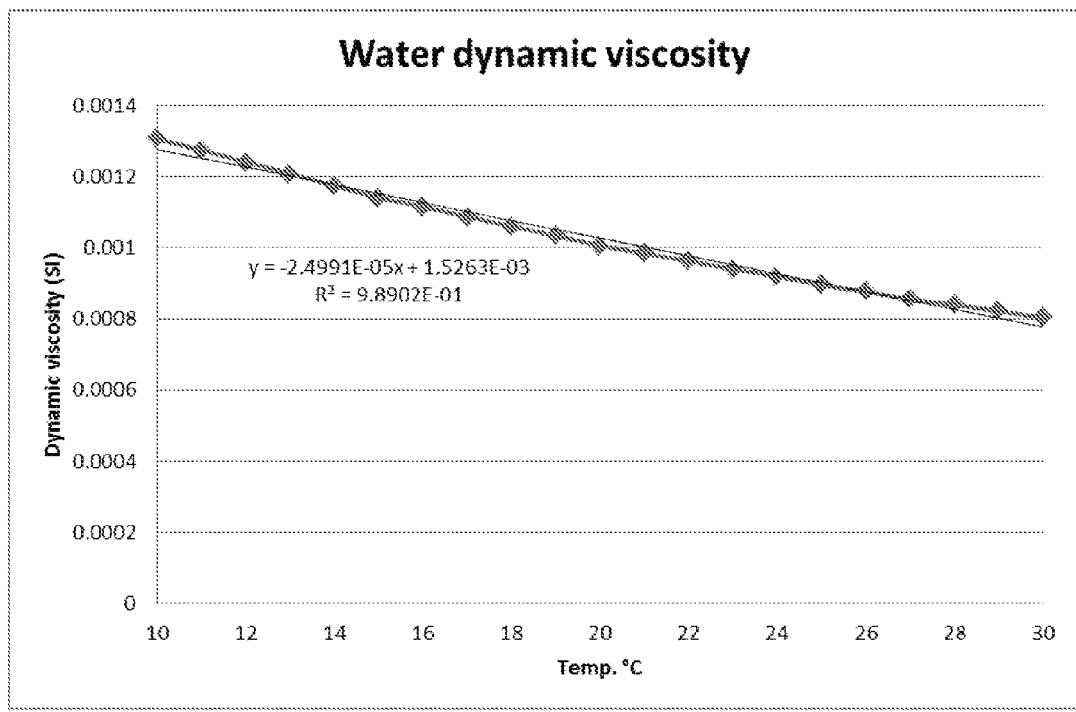

FIG. 6 shows the dynamic viscosity of water between 10° C. and 30° C.

Figure 7:
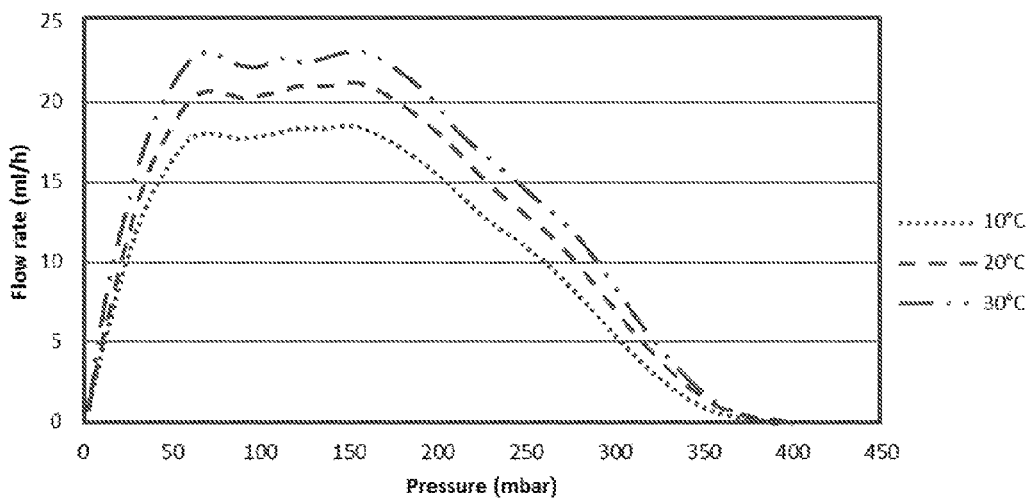

FIG. 7 shows the flow rate of a passive flow regulator without compensation of the temperature.

Figure 8:
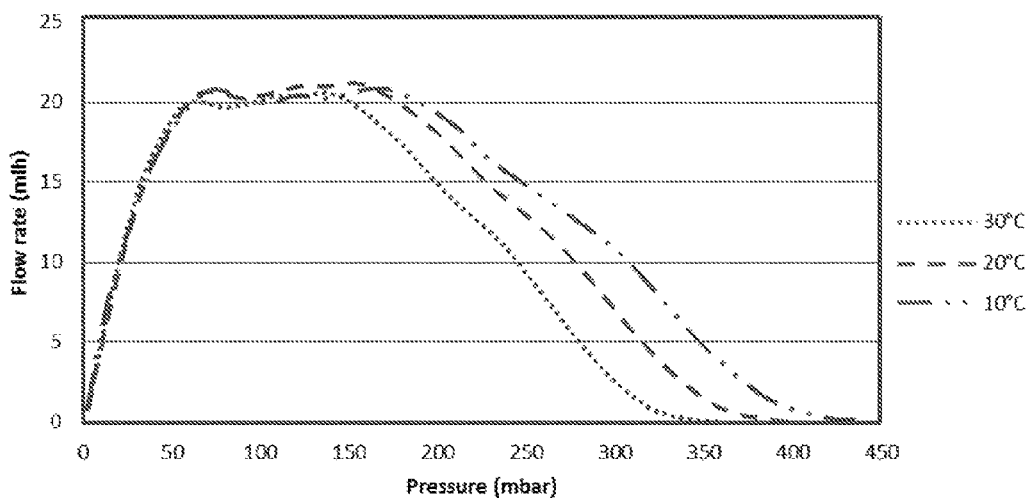

FIG. 8 shows the flow rate of a passive regulator which is autoregulated by the pressure and autoajusted to the temperature.

Figure 9:
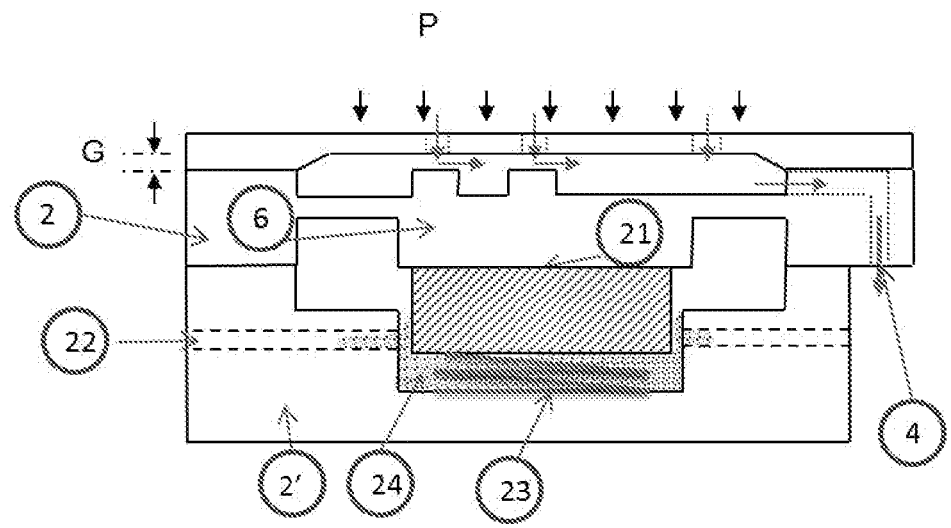

FIG. 9 shows housing with two holes for injecting the glue.

Figure 10:
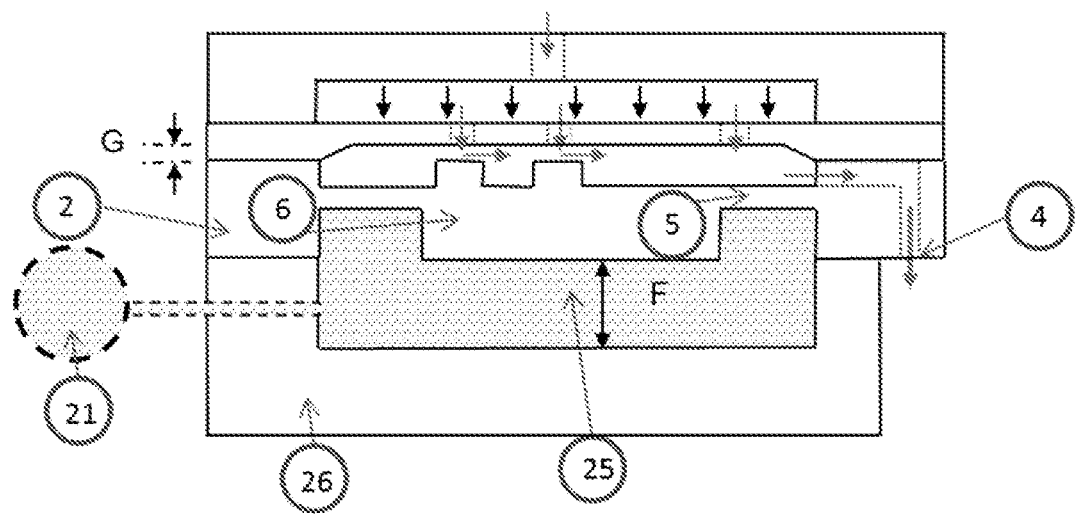

FIG. 10 shows another possible embodiment.

Figure 11:
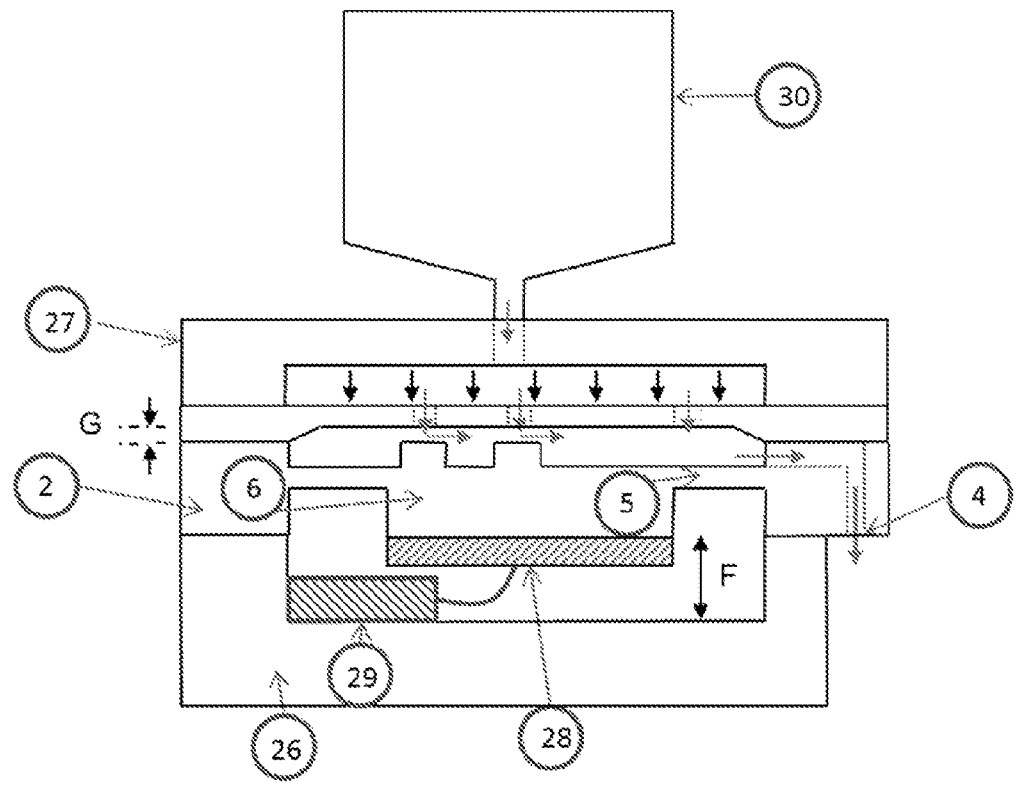

FIG. 11 shows another possible embodiment wherein the adjustment means is a piezo.

Figure 12:
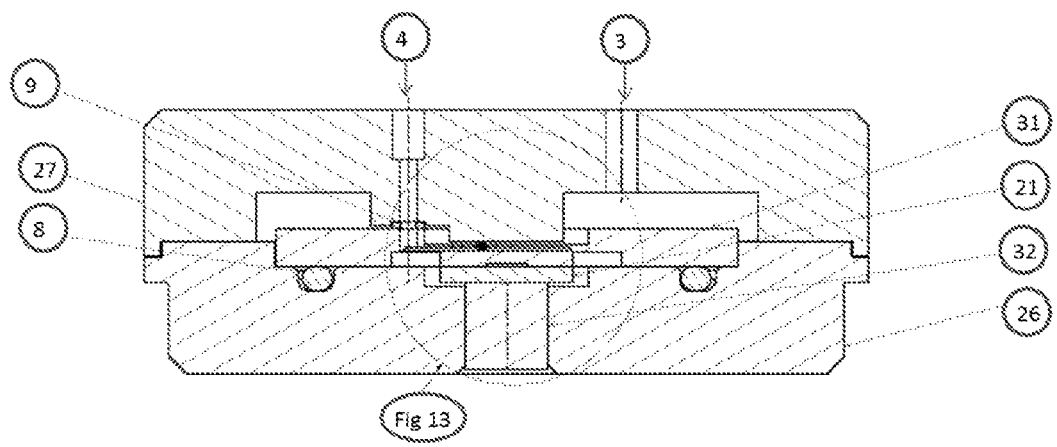

FIG. 12 shows a possible embodiment comprising a regulator into a housing.

Figure 13:
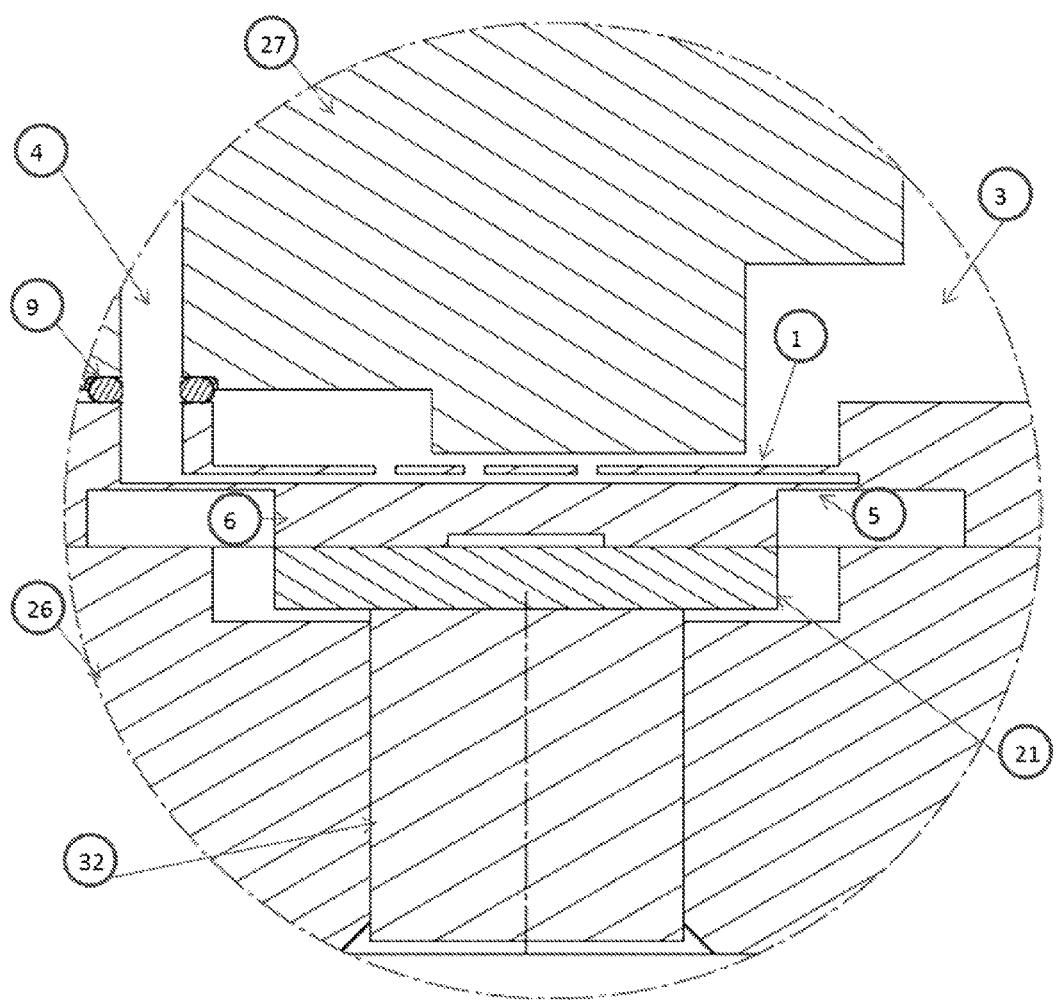

FIG. 13 shows a detailed image of the FIG. 12.

LIST OF ELEMENTS

1 Flexible membrane
1' Flexible membrane
2 Substrate
2' Housing
3 Inlet
4 Outlet
5 Flexible part
6 Rigid part
7 O-ring of the inlet
8 O-ring of the regulator
9 O-ring of the outlet
10 Cavity
11 Lower face of membrane
12 Upper face of membrane
13 Hard ball
14 Flexible blade
15 Circular element
16 Screw
17 Elliptic came
18 Skin
19 Magnet element
20 Magnetic tool
21 Expansible element
22 Hole
23 Spring
24 Glue
25 Cavity
26 Lower part of the housing
27 Upper part of the housing
28 Piezo element
29 Controller
30 Reservoir
31 Regulator
32 Support

DETAILED DESCRIPTION OF THE INVENTION

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and/orientations.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The invention is set forth and characterized in the independent claims, while the dependent claims describe other characteristics of the invention.

According to an embodiment but not limited to, the FIG. 1 show a flow regulator which comprises a substrate (2) on top of which a membrane (1) is tightly fixed. Said regulator further comprises a cavity (10) which is located between said substrate (2) and said membrane (1). The distance between said substrate (2) and said membrane (1) corresponds to the depth of the cavity hereinafter called gap G. Said substrate (2) and/or said membrane (1) have through holes which are at least one inlet hole (3) and one outlet hole (4). Said holes permit the fluid to flow through said regulator. Inlet hole (3) and outlet hole (4) are in direct fluid communication with said cavity (10).

According to the same principle of the passive flow regulator which is disclosed in the US patent applications US 2011/0132480 and US 2012/0316492 which are integrated by reference, said membrane (1) comprises an lower face (11) which faces the cavity (10) and an upper face (12) on which the pressure of the fluid (also called P) is applied. Said membrane (1) is flexible in such a way that said membrane (1) comes into contact with said substrate (2) depending on the pressure of the fluid. Said contact may be total or partial, the main goal of this contact is to increase the fluidic resistance in such a way that the flow can be controlled even if the pressure of said fluid increases. When the pressure of the fluid increases, the depth of the cavity (gap G) decreases until the membrane (1) comes into contact (at least partially) to the substrate (2), thus the fluidic resitance increases for hindering said fluid flow.

The regulator may comprise several inlet holes (3). The holes positions and dimensions are arranged so that the fluid flow rate is passively regulated, depending on the fluid pressure, at least in a range of fluid pressure going from a first and at least a second predefined threshold values.

Figure 1A:
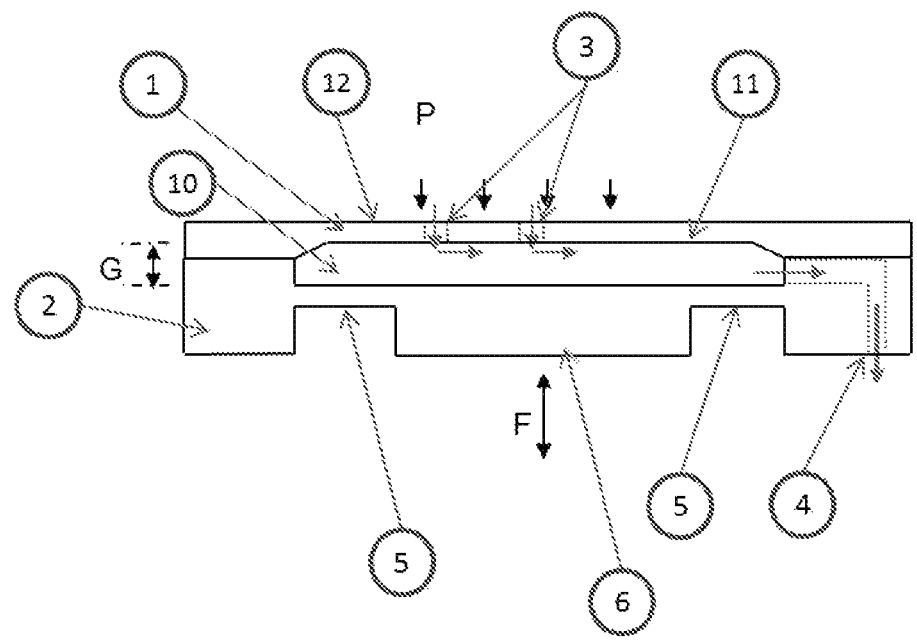
FIG. 1a shows a passive flow regulator with drilled membrane and substrate having a rigid part and a flexible part.
Figure 1B:
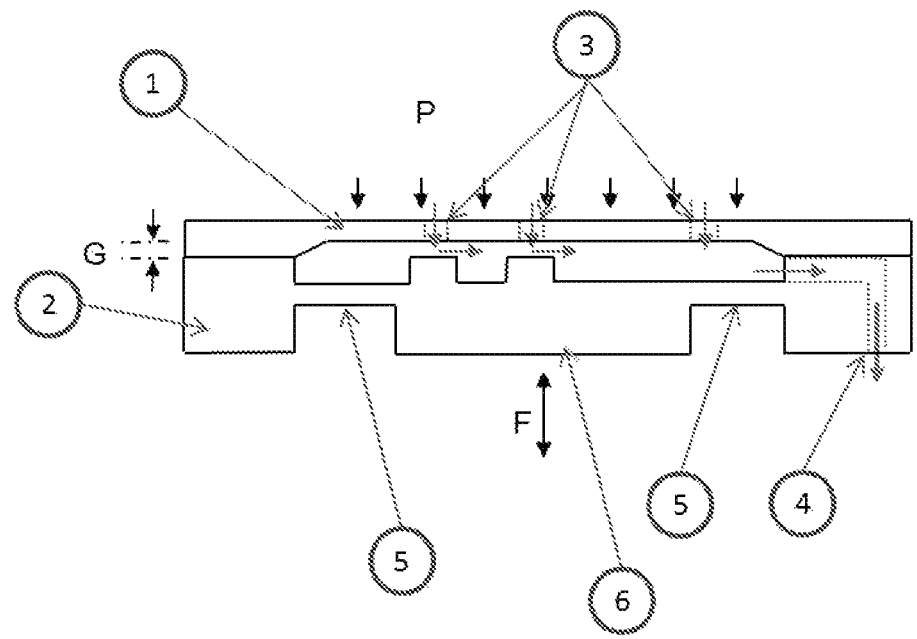
FIG. 1b shows the same embodiment of FIG. 1a but comprising pillars.

The FIG. 1a shows an embodiment without pillar. The FIG. 1b shows another embodiment that comprises at least one pillar. Said pillar may be aligned to the inlet holes and may be located on the membrane and/or the rigid part. The position of the outlet may be located either on the top or the bottom or the side of the substrate or the membrane. Inlet and outlet may be on the same side.

Advantageously, the substrate (2) comprises a rigid part (6) surrounded by a flexible part (5). Due to the flexible part (5), said rigid part (6) is able to move downwardly and/or upwardly. In other words, the rigid part (6) can move to the membrane (1) or move away from the membrane (1) in such a way as to decrease or increase the gap G. Said rigid part may come into contact with said membrane.

In an embodiment, the regulator further comprises an adjustment means designed to move and/or to maintain at least temporarily said rigid part at a given position. Said adjustment means is shown in the FIGS. 2a to 2c and 3a to 3d. In another words, the adjustment means permits applying a force F on the rigid part of substrate to adjust the gap G of the cavity.

Thanks to said adjustment means, the gap G is adjustable, the graph of the FIG. 4 shows the effect of the gap on the flow rate. Thus the changes of few microns around the nominal values of the gap induces an offset of the flow rate plateau while the pressure range of regulation is slightly shifted. The FIG. 5 shows the means flow rate value, in the range of regulation 10 to 40 mbar, as a function of the gap. The linearity of this curve makes possible the use of a spring to adjust the flow rate. To achieve a displacement of only few microns, it is more relevant to control the force on the rigid part and not its displacement.

In an embodiment, the membrane is much more flexible than the substrate. The pressure force transmitted by the membrane after contact with the substrate should be negligible compared to the restoring force of the substrate.

The main difference between the embodiments of the FIGS. 2 and 3 concerns the adjustment means. The adjustment means of the FIG. 2 comprises mechanical elements which may be manually or automatically actuated. Said mechanical element may be controlled by an electronic controller or manually or automatically. While the adjustment means of the FIG. 3 contains an expansible element which has a high coefficient of thermal expansion (for example but not limited to a polymeric rod) in such a way as to move the rigid part depending on the temperature. Said expansible element may be ABS (Acrylonitrile butadiene styrene), Acetal, Acrylic Alumina, Aluminum, Antimony, Arsenic, Barium, Barium ferrite, Benzocyclobutene, Beryllium, Bismuth, Brass, Brick masonry, Bronze, Cadmium, Calcium, Cast Iron Gray, Cellulose acetate (CA), Cellulose acetate butynate (CAB), Cellulose nitrate (CN), Cement, Cerium, Chlorinated polyvinylchloride (CPVC), Chromium, Clay tile structure, Cobalt, Concrete, Constantan, Copper, Corundum, Cupronickel 30%, Diamond, Duralumin, Dysprosium, Ebonite, Epoxy, Erbium, Ethylene ethyl acrylate (EEA), Ethylene vinyl acetate (EVA), Europium, Fluoroethylene propylene (FEP), Gadolinium, Germanium, Glass, Pyrex, Gold, Granite, Gunmetal, Hafnium, Hard alloy K20, Hastelloy C, Holmium, Inconel, Indium, Invar, Iridium, Iron, Kapton, Lanthanum, Lead, Limestone, Lithium, Lutetium, Macor, Magnesium, Manganese, Marble, Masonry, Mercury, Mica, Molybdenum, Monel, Mortar, Neodymium, Nickel, Niobium, Nylon, Oak, Osmium, Palladium, Phenolic resin without fillers, Phosphor bronze, Plaster, Plastics, Platinum, Plutonium, Polyallomer, Polyamide (PA), Polybutylene (PB), Polycarbonate (PC), Polyester, Polyethylene (PE), Polyethylene terephthalate (PET), Polyphenylene, Polystyrene (PS), Polysulfone (PSO), Polyurethane (PUR), Polyvinyl chloride (PVC), Polyvinylidene fluoride (PVDF), Porcelain, Potassium, Praseodymium, Promethium, Quartz, Rhenium, Rhodium, Rubber, Ruthenium, Samarium, Sandstone, Sapphire, Scandium, Selenium, Silicon, Silicon Carbide, Silver, Sitall, Slate, Sodium, Steatite, Steel, Steel Stainless Austenitic, Steel Stainless Ferritic (410), Strontium, Tantalum, Tellurium, Terbium, Terne, Thallium, Thorium, Thulium, Tin, Titanium, Tungsten, Uranium, Vanadium, Vinyl Ester, Wood, Ytterbium, Yttrium, Zinc and/or Zirconium.

The embodiment shown in the FIGS. 3b to 3d comprises both adjustment means mechanical elements and said expansible element. In one embodiment, said adjustment means may be programmable and/or may comprise said expansible element.

In one embodiment, said adjustment means may exert a force F with a spring, e.g. a flexible blade (14) in compression against a hard ball (13) glued on the rigid part (6) as shown in FIG. 2a or a circular element (15) fixed to the flexible blade (14) and in contact with the rigid part (6) as shown in FIG. 2c. The ball (13) or circular element (15) prevents substrate flexure by transmitting no couple.

The force F may be adjusted by the rotation of an elliptic came (17) or a screw (16) in contact directly or not with the rigid part (6) as shown in FIGS. 2b, 2c, 3b. 3c and 3d. Said adjustment means may be fixed to the housing (2') of the regulator.

In the FIG. 2b, the flow regulator is implanted under the skin (18) of the patient, the adjustment means may contain magnetic element (19) which allows adjust the flow with a magnetic tool (20). In one embodiment which uses a system lock disclosed in the patent FR 2721520, wherein a rotor (16) comprises two axially opposed magnets (19) can turn around its rotation axis. The contents of the patent FR 2721520 are incorporated by reference in the present account. The magnetic tool (20) comprises two magnets which is able to slide along a same axis. Said magnets have two positions (locking and unlocking) and are placed in front of the implanted device. The magnets of the magnetic tool (20) and the magnets (19) of the rotor (16) may be coupled in such a way that the patient can change manually the positions of the magnets of the rotor (16) thanks to the magnetic tool (20). Thus, the rotation of the rotor (16) modifies the force of the blade. The magnets are radially opposed with respect to the centre of the rotor. The magnets (19) of the rotor (16) are made of hard magnetic material having the same magnetization orientation and direction. The magnets (19) can slide along the radial axis of the rotor (16). Spring elements in contact with the magnets ensure that the magnets (19) are initially in lock position, preventing any unwanted rotation of the rotor (16). Since both magnets (19) are locked in a given position, the application of an external magnetic field may only unlock one magnet.

In another embodiment not shown, the adjustment means may be a push-pull system which could be made by gluing a flexible blade (14) onto the rigid part (6) and by attaching the spring onto this flexible blade (14). The blocking of the substrate due to a flexure is prevented by the flexibility of the blade attached to the mesa. The spring and the flexible blade can be a single preformed blade.

In other embodiments shown in the FIG. 3, the regulator comprises an adjustment means containing an expansible element (21) which has a high coefficient of thermal expansion in such a way as to move the rigid part (6) depending on the temperature. Said expansible element (21) may be a polymer or plastic rod or other. The variable force is ensured by said element that expands when increases the temperature. Said expansible element may permit the compensating the change of the viscosity of the fluid when the temperature changes. Thus the valves of the system have a fluidic resistance for a given reservoir pressure and when the temperature increases, the device may compensate the reduction of the dynamic viscosity of the liquid. In an embodiment, the expansible element (21) is arranged to be at least partially immersed in the fluid.

The principle of this embodiment is therefore based on the "linearity" of three different phenomena:
1. The viscosity of water (for e.g.) as a function of temperature between 10° C. and 30° C. as shown in FIG. 1
2. The mean regulated flow as a function of the gap between the membrane and the substrate for a given range of pressure
3. The linear expansion of plastic material as a function of temperature The graph of the FIG. 6 shows the water dynamic viscosity and the graph of the FIG. 7 shows the flow regulation by a passive flow regulator without compensation of the temperature.

The flow regulation by the same device but comprising a passive compensation of the thermal effect on viscosity is shown in the graph of the FIG. 8. So the results are conclusive, the expansible element permits to compensate the change of fluid viscosity with temperature. The present document describes the test where the fluid which flows through the regulator is water. But it's the same principle with other liquids, the expansible element being adapted to compensate its own viscosity characteristics. For gas, it is required to take into account the change of density if a specific mass flow is required.

For example but not limited to, the gap is set at 24 μm at 10° C. The effect of temperature increases the length of the rod and reduces the gap of 2 um for 10° C. The rod comprises a polyethylene part of 1.2 mm long and 5 mm in diameter. The use of expansible element (21) having a CTE as high as $2E\text{-}4° C.^{-1}$ is particularly relevant to get the substrate deflection for limited rod dimension. For a range of 20° C., the total elongation of the rod could be up to 20 microns. A rod in polyethylene having a length of 6 mm and a diameter of 5 mm is suitable to get a substrate displacement of about 1 μm per ° C. for a substrate having a restoring force of 0.5 N/um. The pressure forces transmitted by the membrane in contact with the substrate are at least two orders of magnitude lower than the force due to thermal expansion, for a typical pressure of 200 mbar.

The FIG. 9 shows the housing (2') with at least one hole (22) which permits to inject the glue (24) for fixing of the expansible element (21) to the housing (2') without generate stress to the rigid part (6) of the substrate (2) during the assembly.

For example, the expansible element (21) has ideally a clip that is used to assemble. After thermowelding of the top and the bottom parts of the device the expansible element (21) is unclipped and the spring (23) ensures that the expansible element (21) is well in contact with the rigid part (6). Glue (24) is then introduces into a hole (22) located in the bottom or side of the housing (2'). This glue (24) makes an anchor with the drilled rod and prevents vertical displacement due to shrinkage of the glue during the polymerisation process. Polymerisation is preferably performed at a given temperature which may be the application temperature of the regulator, in order to ensure that the expansible element (21) is always in compression. This configuration is compatible with the use of an anti-tilting ball.

In other case, the device may be used in "push-pull" mode by gluing a flexible blade on the substrate (2), said flexible blade being molded into a PE rod. No spring is necessary in this case.

The regulator may be implanted in a patient or used outside of the patient for instance to control the flow rate of a perfusion. The regulator may be arranged in a housing. When the regulator is used outside, the expansible element used as the adjustment means is particularly interesting. So when the temperature of the fluid varies, the regulator can adjust the position of the rigid part of the substrate in such a way that the expansible element permits to compensate the change of viscosity of the fluid when the temperature changes.

In one embodiment shown in FIG. 10, said regulator comprises a cavity (25) between at least a part of the substrate (2) and the lower part of the housing (26). Said cavity (25) may comprise means for maintaining a fluid therein between a first pressure and a second pressure. For example, said cavity (25) may be pressurized by a fluid (Freon or other) or by a mechanical means (for instance a fluid pump) or other means (for example heater means which heat the fluid in such a way as to expand the fluid).

In other embodiment, said cavity (25) may be ventilated in such a way as to prevent a displacement of the rigid part in a non-controlled manner. So the housing and/or the regulator may comprise a vent.

The pressure of the fluid in this cavity (25) may be controlled and/or monitored.

In one embodiment shown in FIG. 11, the adjustment means is controlled by electronically means. For instance, the adjustment means may be a piezo electric element (28) which moves the rigid part (6) of the substrate (2) depending on the tension applied by a controller (29). So the fluid contained in a reservoir (30) flows through the inlet of the upper part (27) of the housing and then through the regulator to reach the outlet (4). Said fluid applies a force on the membrane of the regulator in such a way as to deflect the membrane depending on the pressure of the fluid upstream of the regulator. So the fluid flow is auto regulated. Further the adjustment means may apply a force on the rigid part of the substrate in such a way as to adjust the flow. So the fluid flow is also adjusted accurately.

In one possible embodiment, the FIG. 12 discloses the regulator (31) in its housing comprising an upper part (27) and a lower part (26). In this embodiment the upper part comprises an inlet (3) and an outlet (4). An O-ring (9) is arranged in the outlet pathway between the regulator (31) and the housing in such a way as to obtain optimum sealing and to prevent any exchange of fluid between the outlet and the inlet upstream the regulator. Another O-ring (8) is arranged between the lower part (26) of the housing and the regulator (31) to prevent that the fluid which flows through the regulator (31) passes under the regulator in the cavity between the lower face of the substrate and the lower part of the housing.

The FIG. 13 is an enlarged image of center of the FIG. 12. The rigid part (6) of the substrate and/or the expansible element (21) may comprise a cavity between said both elements. A drop of glue may be disposed in this cavity to fix the rigid part (6) to the expansible element (21). Thanks to this cavity, the glue remains in this cavity and cannot flow around said both elements. The support (32) may be fixed to the expansible element (21) and one of aims of this support is to adjust the position of the rigid part (6). Said support may be fixed to the lower part (26) of the housing.

An assembly process may comprise the following steps:
Providing one of the regulators described above, a lower part of housing and an adjustment element,
Arranging the adjustment element on the lower part of the housing
Arranging and fixing the regulator on the adjustment element
Said steps may be successive.

If the adjustment element is an expansible element, the assembly may be done at a determined temperature for instance 20° C. or the rated operating temperature.

A support (32) may be used to adjust the positioning of the adjustment element on the lower part (26) of the housing. Said adjustment may be done before or after the arranging of the regulator on the lower part of the housing. After said adjustment, said support may be fixed to the lower part of the housing or may be used as a second adjustment element. Said support may be a screw, a rode or other.

The upper part (27) of the housing or the regulator may comprise mechanical stop means in such a way as to limit the deflecting of the membrane. Said mechanical stop means is arranged on the membrane and the upper face of the membrane may be designed to come into contact with said mechanical stop means. Said membrane and/or said mechanical stop means may comprise an anti-bonding layer. Said mechanical stop means may be a pillar or other elements. Said mechanical stop means may be designed and/or arranged in such a way as to:

permit that the fluid flows through at least one hole of the membrane, and/or stop the flow when the rigid part of the substrate is in a predetermined position.

The priming method may comprise the following steps:
Providing one of the regulators described above
Introducing a fluid by the outlet pathway
Flowing the fluid to reach the input During the priming process as described above, if the regulator and/or the upper part of the housing comprise mechanical stop means, the membrane may deflect so far as to come into contact with said mechanical stop means. So the fluid may be introduced with a determined flow rate and/or a determined pressure without damage the membrane.

The rigid part of the substrate and/or the flexible part of the membrane may be substantially circular. The diameter of said rigid part may be equal to, smaller than or greater than the diameter of said flexible part of the membrane. Said diameters may be comprised between 0 mm to 500 mm, preferentially between 5 mm to 20 mm. The rigid part of the substrate is surrounded by the flexible part of the substrate which may be substantially circular. So said flexible part forms a ring. The interior diameter of said ring may be equal to the diameter of said rigid part and the exterior diameter of said ring may be equal to, smaller than or greater than the diameter of said flexible part of the membrane. Said exterior diameter of said ring may be comprised between 0.1 mm to 1000 mm, preferentially between 5 mm to 30 mm.

The manufacturing process comprises the following step:
Providing a first wafer comprising an upper face and a lower face
Depositing a mask on at least one of said faces
Using a anisotropic etch to pattern at least one holes through the first wafer
Providing a second wafer comprising an upper face and a lower face
Depositing a mask on at least one of said faces
Using a anisotropic etch on the lower face of the second wafer to pattern the flexible part
Depositing an anti-bonding layer on a part of the lower face of the first wafer and/or on a part of the upper face of the second wafer
Depositing a bonding layer on a part of the lower face of the first wafer and/or on a part of the upper face of the second wafer such as parylene
Arranging the first structured wafer on the second structured wafer The steps 1 to 3 and/or 4 to 6 may be successive. The first and/or the second wafer may be made of a SOI (Silicon On Insulator) and at least one etch is done until the insulator layer.

Furthermore, the manufacturing process may comprise at least one additional step:
Using an anisotropic etch to pattern the outlet
Using an anisotropic etch on the upper face of the second wafer to pattern at least one pillar
Using an anisotropic etch to pattern the flexible part of the first wafer
Using an isotropic etch to remove the mask of the Wafers
Using an isotropic etch to remove the insulator of the SOI Wafer
Using an etch to selectively remove the bonding layer
Using an isotropic etch to clean said wafer.

The invention claimed is:

1. A flow regulator for adjusting a flow of a fluid, comprising:
a substrate having a rigid part surrounded by a flexible part, the flexible part configured to move up and down relative to the rigid part;
a flexible membrane arranged to face the substrate;
a cavity formed between the substrate and the flexible membrane;
an inlet in fluid communication with the cavity; and
an outlet formed in at least one of the flexible membrane and the substrate, the outlet in fluid communication with the cavity,
wherein a surface of the flexible membrane facing away from the cavity is configured to be exposed a pressure of the fluid, the flexible membrane configured to contact the substrate via the cavity depending on the pressure of the fluid,
wherein the flexible part of the substrate is configured to allow the rigid part to move up and down relative to the flexible part.

2. The flow regulator according to claim 1, further comprising:
an adjustment device configured to actuate the rigid part of the substrate, to at least one of move and maintain the rigid part at a given position.

3. The flow regulator according to claim 2, wherein the adjustment device is configured to be manually actuated, automatically actuated, or electronically actuated.

4. The flow regulator according to claim 2, wherein the adjustment device includes an expansible element having a thermal expansion coefficient to move the rigid part depending on a temperature.

5. The flow regulator according to claim 4, wherein the expansible element is configured to compensate the flow of the fluid depending on the temperature.

6. The flow regulator according to claim 4, wherein the expansible element is configured to maintain the flow of the fluid independently of a variation of the temperature.

7. The flow regulator according to claim 4, wherein the expansible element is configured to adjust the flow depending on the temperature.

8. The flow regulator according to claim 2, wherein the actuation of the adjustment device is programmable.

9. The flow regulator according to claim 2, wherein the adjustment device includes a flexible blade, a screw, a elliptic came, or a magnetic element.

10. The flow regulator according to claim 2, further comprising:
a housing, the adjustment device arranged between the housing and the flexible part of the substrate.

11. The flow regulator according to claim 1, wherein the inlet is formed in the flexible membrane and is aligned with a location of the rigid part.

12. The flow regulator according to claim 1, further comprising:
a pillar located in the cavity, a height of the pillar being smaller than a height of the cavity.

13. The flow regulator according to claim 12, wherein the inlet is formed in the flexible membrane and the pillar is aligned with the inlet to form a valve.

14. The flow regulator according to claim 13, wherein the pillar has a width that is larger than a width of the inlet.

15. The flow regulator according to claim 1, wherein the adjustment device includes a circular or semi-circular element configured to prevent a flexure of the rigid part of the substrate.

16. A flow regulator for adjusting a flow of a fluid, comprising:
a moving means having a rigid part surrounded by a flexible part, the flexible part moving up and down relative to the rigid part;
a flexible means arranged to face the moving means;
a cavity formed between the moving means and the flexible means;
an inlet in fluid communication with the cavity; and
an outlet formed in at least one of the flexible means and the moving means, the outlet in fluid communication with the cavity,
wherein a surface of the flexible means facing away from the cavity is configured to be exposed a pressure of the fluid, the flexible means for contacting the substrate via the cavity depending on the pressure of the fluid,
wherein the flexible part of the moving means is configured to allow the rigid part to move up and down relative to the flexible part.

17. The flow regulator according to claim 16, further comprising:
an adjustable means for actuating the rigid part of the moving means, to at least one of move and maintain the rigid part at a given position.

18. The flow regulator according to claim 17, wherein the adjustable means includes an expansible means having a thermal expansion coefficient for moving the rigid part depending on a temperature.

19. The flow regulator according to claim 18, wherein the expansible means maintains the flow of the fluid through the cavity independently of a variation of the temperature.

20. A flow regulator for adjusting a flow of a fluid, comprising:
a moving means having a rigid part surrounded by a flexible part, the flexible part moving up and down relative to the rigid part;
a flexible means arranged to face the moving means;
a cavity formed between the moving means and the flexible means;
an inlet in fluid communication with the cavity;
an adjustable means for actuating the rigid part of the moving means, to at least one of move and maintain the rigid part at a given position; and
an outlet formed in at least one of the flexible means and the moving means, the outlet in fluid communication with the cavity,
wherein a surface of the flexible means facing away from the cavity is configured to be exposed a pressure of the fluid, the flexible means for contacting the substrate via the cavity depending on the pressure of the fluid, and
wherein the adjustable means includes an expansible means having a thermal expansion coefficient for moving the rigid part depending on a temperature.

* * * * *